United States Patent [19]

Ayad

[11] Patent Number: 5,616,336
[45] Date of Patent: Apr. 1, 1997

[54] METHOD OF COMBATTING INSECT EGGS AND OVICIDAL COMPOSITIONS

[75] Inventor: Hafez M. Ayad, Cary, N.C.

[73] Assignee: Rhone-Poulenc Inc., Research Triangle Park, N.C.

[21] Appl. No.: 436,835

[22] Filed: May 8, 1995

Related U.S. Application Data

[63] Continuation of Ser. No. 207,903, Mar. 7, 1994, abandoned, which is a continuation of Ser. No. 891,848, Jun. 1, 1992, abandoned.

[51] Int. Cl.$^6$ .................................................. A01N 25/04
[52] U.S. Cl. ........................................ 424/405; 514/357
[58] Field of Search ............................ 424/405; 514/357

[56] References Cited

FOREIGN PATENT DOCUMENTS 1516113   6/1978   United Kingdom .

OTHER PUBLICATIONS

Brighton Crop Protection Conf.—Pests D15: 1992(1) 89–96 Takahashi et al.

*Primary Examiner*—Neil S. Levy
*Attorney, Agent, or Firm*—Morgan & Finnegan, L.L.P.

[57] ABSTRACT

A method of protecting a crop by killing eggs of insects, or insects at the egg stage, the insects being detrimental to the crop, said method comprising applying to a locus where the eggs of insects are located or are expected to be located or are expected to be going to be located an effective amount of a compound of formula (I), or a salt thereof, $$R_1-X-N(R_2)-C(R_3)=Z-R_4 \qquad (I)$$

wherein R1 represents an optionally substituted 5–6 membered aromatic hetero ring containing nitrogen atom, except a non-substituted 2-pyridyl;

X represents an optionally substituted alkylene or alkylidene;

R2 represents hydrogen, carbamoyl, mono or di alkyl carbamoyl, thiocarbamoyl, mono or di C1–5 alkylthiocarbamoyl, sulfamoyl, mono or di C1–5 alkylsulfamoyl, an optionally substituted alkyl, alkenyl or alkynyl, an optionally substituted cycloalkyl or cycloalkenyl, optionally substituted aryl or —Y—R5;

Y represents O, S(O)n, CO, CS or CO2;

n represents 0, 1 or 2;

R5 represents a hydrogen, optionally substituted alkyl, alkenyl or alkynyl, optionally substituted cycloalkenyl or aryl;

R3 represents a hydrogen, an optionally substituted alkyl, alkenyl or alkynyl, optionally substituted cycloalkyl or cycloalkenyl;

R4 represents a cyano or a nitro, and

Z represents CH or N.

2 Claims, No Drawings

METHOD OF COMBATTING INSECT EGGS AND OVICIDAL COMPOSITIONS

This is a continuation of application Ser. No. 08/207,903, filed on Mar. 7, 1994, now abandoned, which is a continuation of application Ser. No. 07/891,848, filed on Jun. 1, 1992, abandoned.

BACKGROUND OF THE INVENTION

1. Field of the Invention

This invention relates to a new method of combatting insects at the egg level of development, especially eggs of the tobacco budworm (*Heliothis virescens*; TBW in the abreviated form) at a locus at which there is growing a crop, especially a plantation crop.

The invention relates also to ovicidal compositions used in the invention.

A particular problem among those which farmers have to face is the destruction of cotton fibers by tobacco budworm. This problem is a very important problem because the larvae insect lives a very short time upon the leaves, e.g. about one or two days, and it spends most of its life in the cotton boll where it is protected from outside aggression such as the pesticide action. Thus, it is very important to reach the tobacco budworm at the egg stage before any damage is made to the crop. Thus the invention is also directed to a method of protecting cotton crop.

2. Discussion of the Prior Art

Many insecticides are well known as active ingredients to protect plants against insects. However the compounds which are recommanded purely for their ovicidal action are rather rare, and those which have both an insecticidal and an ovicidal action are also rather rare.

From the activity of a compound on insects (adults or larvae), nothing can be deduced regarding the activity on eggs. For example, insecticides such as carbaryl or phosphate insecticides are not ovicidal. Pyrethroids are not ovicidal either; if they have been sometimes considered as ovicidal, it is just because they are able to kill the larvae when going out from the eggs, but this is not a true ovicidal action. Thiodicarb is considered as having both an ovicidal and an insecticidal action, but it is rather an exception.

Thus, insecticides have been described in patent application WO 91/04965 but it is not possible to know whether they have any ovicidal action for the hereabove given reasons.

SUMMARY OF THE INVENTION

An object of the invention is to provide a method of protecting crop by killing eggs of insects, or insects at the egg stage, whereby an effective amount of a compound of hereafter given formula (I), or a salt thereof, is applied to a locus where eggs of insects are located or are supposed to be located or to be going to be located. The insects whose eggs are killed according to the invention are especially insects which are detrimental to the crop. Another object of the invention is an ovicidal composition comprising an effective amount of active ingredient which is a compound of formula (I), or a salt thereof.

DETAILED DESCRIPTION OF THE INVENTION

Formula (I) represents compounds of the formula:

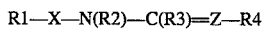  (I)

wherein R1 represents an optionally substituted 5–6 membered aromatic hetero ring containing nitrogen atom, except a non-substituted 2-pyridyl;

X represents an optionally substituted C1–3 alkylene or alkylidene;

R2 represents a hydrogen, a carbamoyl, a mono or di C1–5 alkyl carbamoyl, a thiocarbamoyl, a mono or di C1–5 alkylthiocarbamoyl, a sulfamoyl, a mono or di C1–5 alkylsulfamoyl, an optionally substituted C1–5 alkyl, an optionally substituted C2–5 alkenyl, an optionally substituted C2–5 alkynyl, an optionally substituted C3–8 cycloalkyl, an optionally substituted C3–8 cycloalkenyl, an optionally substituted aryl or —Y—R5;

Y represents O, S(O)n, CO, CS or CO2;

n represents 0, 1 or 2;

R5 represents a hydrogen, an optionally substituted C1–5 alkyl, an optionally substituted C2–5 alkenyl, an optionally substituted C2–5 alkynyl, an optionally substituted C3–8 cycloalkenyl or an optionally substituted aryl;

R3 represents a hydrogen, an optionally substituted C1–5 alkyl, an optionally substituted C2–5 alkenyl, an optionally substituted C2–5 alkynyl, an optionally substituted C3–8 cycloalkyl or an optionally substituted C3–8 cycloalkenyl;

R4 represents a cyano or a nitro, and

Z represents CH or N.

The present invention provides a method of protecting a crop by combatting eggs of insects susceptible to damage the said crop whereby an effective amount of a compound of formula (I), or a salt thereof, is applied at a locus where there are eggs or where eggs are expected to be present or where eggs are expected to be going to be present.

According to the invention it has also been found ovicidal compositions which comprise an effective amount of a compound of formula (I) or a salt thereof.

The present invention provides a method of protecting a crop by combatting eggs of insects susceptible to damage the said crop whereby an effective amount of an ovicidal composition as already defined is applied at a locus where there are eggs or where eggs are expected to be present or where eggs are expected to be going to be present.

Another feature of the present invention is that an ovicidal composition is applied at a locus where a crop is growing, especially a plantation crop, more especially cotton.

The method of the invention is particularly appropriate to kill or control the following insects at the egg stage: tobacco budworm (*Heliothis virescens*), Mexican bean beetle (*Epilachna varivestis*), Colorado potato beetle (*Leptinotarsa decemlineata*).

The method of the invention is especially advantageous to kill tobacco budworms, at the egg stage, which are resistant to pyrethroids.

The method of the invention is particularly appropriate to protect cotton crop from tobacco budworm or pyrethroid resistant tobacco budworm, beans and soybean from Mexican bean beetle, potato crop from Colorado potato beetle.

Preferred active ingredients which may be used in the invention are those wherein:

R1 is halopyridyl, more preferably a 6-halo pyrid 3-yl.
R3 is H or alkyl.
R2 is H or alkyl, X is CH2, Z is =N—.

The preparation of compounds of formula (I), or a salt thereof, may be made according to any process described in patent application WO 91/04965, which corresponds to U.S.

Pat. No. 5,304,566 or other process according to the knowledge of a man skilled in the art of chemical synthesis. The disclosure of WO 91/04965, which corresponds to U.S. Pat. No. 5,304,566 is in toto incorporated herein by reference.

By the term "eggs" as used in this specification, it is to be understood eggs which are in their simple state laid upon the soil or on the plant or eggs which are inside pregnant insect. Most of the eggs which are to be killed according to the present invention are eggs upon leaves, so that the method whereby an active ingredient of formula (I), or a salt thereof, is applied is also a treatment of leaves of crops.

The invention enables compounds of formula (I), or salts thereof, to combat insects, especially the tobacco budworm, at the egg stage before they reach the damaging later stages. Thus, compounds of formula (I), or salts thereof, are applied to the locus to be treated before substantial infestation with tobacco budworm larvae occurs.

For instance, on cotton plants, an ovicidal composition comprising a compound of formula (I), or a salt thereof, should be applied to eggs before applying it to the larval stage, preferably 4 to 7 days before one would first apply such a composition to the larval stage of tobacco budworm.

The ovicidal compositions of the invention may be applied once, or more than once. Thus, for some crops one may apply the ovicidal compositions periodically through the insects season. Usually ovicidal compositions according to the invention are applied to the crop area at a rate of 0.04 to 2 kg/ha of active ingredient, preferably 0.1 to 1 kg/ha.

Ovicidal compositions according to the invention may be applied in a manner which is safe for the crop.

The ovicidal concentrated compositions according to the invention may be in the form of a solid, e.g. dusts or granules or wettable powders, or, preferably, in the form of a liquid, such as an emulsifiable concentrate or a true solution. The concentrated compositions are the compositions which are commercialized or transported or stored. For application to plant they are normally diluted in water and applied in such a diluted form. The diluted form are part of the invention as well as the concentrated forms.

The concentrated ovicidal compositions of the inventions contain generally from 0.001 to 90% of active ingredient of formula (I), or a salt thereof. A concentrate may contain from 5 to 90% of active ingredient. Parts and percentages in this specification are by weight unless otherwise indicated.

The ovicidal compositions may also contain all kind of compatible surface active agent and/or carrier. The agriculturally acceptable carrier may be solid or liquid. The composition may further contain a fertilizer.

The compounds of formula (I), or a salt thereof, may be used in sequence or admixture, particularly admixtures with another pesticide e.g. an insecticide, acaricide or fungicide.

The ovicidal compositions may be prepared by admixing the ingredients.

The invention is illustrated by the following test examples.

EXAMPLE 1

(6-Cl pyrid 3-yl)—CH2—N(CH3)—C(CH3)=N—CN was dispersed in a mixture of acetone/surfactant/dimethylformamide and then diluted in water.

Strips of cheese cloth which contained about 30 to 40 one day old eggs of tobacco budworm were used. They were eggs of tobacco budworm non resistant to pyrethroids.

The aqueous dispersion of active ingredient was sprayed upon the eggs. The application condition were such that a 1000 ppm concentration corresponds to an application rate of 188 g/ha on the crop.

The observation of the obtained results was made three days after spraying. The dead eggs are brown and do not hatch (they normally hatch about 3 to 4 days after being laid down).

A lethal dose killing 90% of the eggs was found at 1000 ppm.

A lethal dose killing 50% of the eggs was found at 230 ppm.

EXAMPLE 2

Example 1 was repeated, except that eggs of pyrethroids resistant tobacco budworm were used.

A lethal dose killing 64% of the eggs was found at 250 ppm.

EXAMPLE 3

(6-Cl pyrid 3-yl)—CH2—N(CH3)—C(CH3)=N—CN was dispersed in a mixture of acetone/surfactant/dimethylformamide and then diluted in water.

Strips of bean plant leaves bearing about 65 one day old eggs of Mexican bean beetle were used.

The aqueous dispersion of active ingredient was sprayed upon the eggs. The application condition were such that a 1000 ppm concentration corresponds to an application rate of 188 g/ha on the crop.

The observation of the obtained results was made three days after spraying. The dead eggs are brown and do not hatch (they normally hatch about 7 days after being laid down).

A lethal dose killing 100% of the eggs was found at 250 ppm.

EXAMPLE 4

(6-Cl pyrid 3-yl)—CH2—N(CH3)—C(CH3)=N—CN was dispersed in a mixture of acetone/surfactant/dimethylformamide and then diluted in water.

Strips of egg plant leaves bearing about 20 one day old eggs of Colorado potato beetle were used. Eggs of beetles resistant as well as non resistant to pyrethroids were used.

The aqueous dispersion of active ingredient was sprayed upon the eggs. The application condition were such that a 1000 ppm concentration corresponds to an application rate of 188 g/ha on the crop.

The observation of the obtained results was made three days after spraying. The dead eggs are brown and do not hatch (they normally hatch about 5 days after being laid down).

A lethal dose killing 100% of the eggs of both type of beetles was found at 250 ppm.

I claim:

1. An ovicidal composition for killing the eggs of tobacco bud worm, Mexican bean beetle or Colorado potato beetle comprising a) an ovicidally effective amount of a compound or salt of the formula:

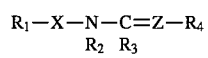

wherein:

$R_1$ is halopyridyl or 6-halopyrid-3-yl;

$R_2$ and $R_3$ are hydrogen or $C_1$–$C_5$ alkyl;

$R_4$ is cyano;

X is $CH_2$; and

Z is N;

b) a compatible surface active agent to aid in the coating of the ovicidal composition on said insect eggs; and c) an agriculturally acceptable carrier for delivering said ovicidal composition to said eggs wherein the composition comprises a mixture of acetone/surfactant/dimethylformamide which is diluted with water.

2. The composition of claim 1, wherein the compound is (6-Cl-pyrid-3-yl)—$CH_2$—$N(CH_3)$—$C(CH_3)$=N—CN.

* * * * *